United States Patent
Zhang et al.

(10) Patent No.: US 8,428,697 B2
(45) Date of Patent: Apr. 23, 2013

(54) "BLURRED TEMPLATE" APPROACH FOR ARRHYTHMIA DETECTION

(75) Inventors: Xin Zhang, New Brighton, MN (US); Mark L. Brown, North Oaks, MN (US); Xusheng Zhang, Shoreview, MN (US); Jeffrey M. Gillberg, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 568 days.

(21) Appl. No.: 12/357,868

(22) Filed: Jan. 22, 2009

(65) Prior Publication Data
US 2010/0185109 A1  Jul. 22, 2010

(51) Int. Cl.
*A61B 5/04* (2006.01)

(52) U.S. Cl.
USPC .............................. 600/509; 600/508; 607/5

(58) Field of Classification Search .......... 600/508–509; 607/5
See application file for complete search history.

(56) References Cited

U.S. PATENT DOCUMENTS

| | | | |
|---|---|---|---|
| 5,000,189 A | 3/1991 | Throne et al. | |
| 5,117,824 A | 6/1992 | Keimel et al. | |
| 5,273,049 A | 12/1993 | Steinhaus et al. | |
| 5,545,186 A | 8/1996 | Olson et al. | |
| 6,308,095 B1 | 10/2001 | Hsu et al. | |
| 6,393,316 B1 | 5/2002 | Gillberg et al. | |
| 6,430,435 B1 | 8/2002 | Hsu et al. | |
| 6,745,068 B2 | 6/2004 | Koyrakh et al. | |
| 6,915,158 B2 | 7/2005 | Bjorling | |
| 6,959,212 B2 | 10/2005 | Hsu et al. | |
| 7,062,315 B2 | 6/2006 | Koyrakh et al. | |
| 7,103,404 B2 | 9/2006 | Stadler et al. | |
| 7,167,747 B2 | 1/2007 | Gunderson et al. | |
| 7,242,978 B2 | 7/2007 | Gillberg et al. | |
| 7,430,446 B2 | 9/2008 | Li | |
| 2001/0056245 A1 | 12/2001 | Mlynash et al. | |
| 2004/0093035 A1* | 5/2004 | Schwartz et al. ................ | 607/5 |
| 2005/0137485 A1 | 6/2005 | Cao et al. | |
| 2005/0234358 A1 | 10/2005 | Cao et al. | |
| 2006/0074331 A1 | 4/2006 | Bocek | |
| 2006/0095083 A1 | 5/2006 | Zhang et al. | |
| 2006/0111747 A1 | 5/2006 | Cazares et al. | |
| 2006/0111751 A1 | 5/2006 | Cazares et al. | |
| 2006/0247703 A1 | 11/2006 | Gutierrez | |
| 2006/0270937 A1 | 11/2006 | Cao et al. | |

(Continued)

FOREIGN PATENT DOCUMENTS

| | | |
|---|---|---|
| EP | 1504788 | 2/2005 |
| WO | 2004075983 | 9/2004 |
| WO | 2007078666 | 7/2007 |
| WO | 2008073266 | 6/2008 |

OTHER PUBLICATIONS

Saul E. Greenhut, Separation of Ventricular Tachycardia From Sinus Rhythm Using a Practical, Real-Time Template Matching Computer System, PACE, vol. 15, November, Part II 1992.

(Continued)

*Primary Examiner* — Nicole F Lavert
(74) *Attorney, Agent, or Firm* — Michael C. Soldner

(57) ABSTRACT

An implantable medical device and associated method sense cardiac signals for deriving a template representing a known EGM waveform morphology and for classifying an unknown waveform morphology. A boundary of the template, offset from the template, is computed and compared to an unknown waveform morphology for classifying the unknown waveform morphology.

27 Claims, 9 Drawing Sheets

U.S. PATENT DOCUMENTS

| | | |
|---|---|---|
| 2006/0281998 A1 | 12/2006 | Li |
| 2007/0142736 A1 | 6/2007 | Cazares et al. |
| 2007/0142737 A1 | 6/2007 | Cazares |
| 2007/0149890 A1 | 6/2007 | Li et al. |
| 2007/0239217 A1 | 10/2007 | Cazares |
| 2007/0275276 A1 | 11/2007 | Gillberg et al. |
| 2007/0276276 A1 | 11/2007 | Gillberg et al. |
| 2008/0077030 A1 | 3/2008 | Ostroff et al. |
| 2008/0140143 A1 | 6/2008 | Bocek |
| 2008/0154322 A1 | 6/2008 | Jackson et al. |
| 2008/0269624 A1 | 10/2008 | Gillberg et al. |

OTHER PUBLICATIONS (PCT/US2010/021580) PCT Notification of Transmittal of the International Search Report and the Written Opinion of the International Searching Authority, Mailed Apr. 15, 2010, 10 pages.

\* cited by examiner

"BLURRED TEMPLATE" APPROACH FOR ARRHYTHMIA DETECTION

TECHNICAL FIELD

The disclosure relates generally to implantable medical devices and, in particular, to an implantable device and associated method using cardiac electrogram (EGM) morphology templates for detecting arrhythmias.

BACKGROUND

Some implantable cardioverter defibrillators (ICDs) are configured to evaluate the morphology of an unknown cardiac EGM waveform in the detection and discrimination of cardiac arrhythmias. The morphology of the unknown waveform may be compared to a previously determined morphology template corresponding to a known waveform for classifying the unknown waveform based on whether the unknown waveform "matches" the known template. The usefulness of such comparisons are dependent on the quality of the sensed signal, the quality of the template, and the methods used to extract morphological features of the waveforms. Clipped QRS signals and double-peaked QRS signals are examples of sensed signals of unknown waveforms that are particularly challenging to classify accurately using template comparison algorithms. Methods are needed for accurate waveform classification based on morphology template comparisons.

DETAILED DESCRIPTION

Figure 1:
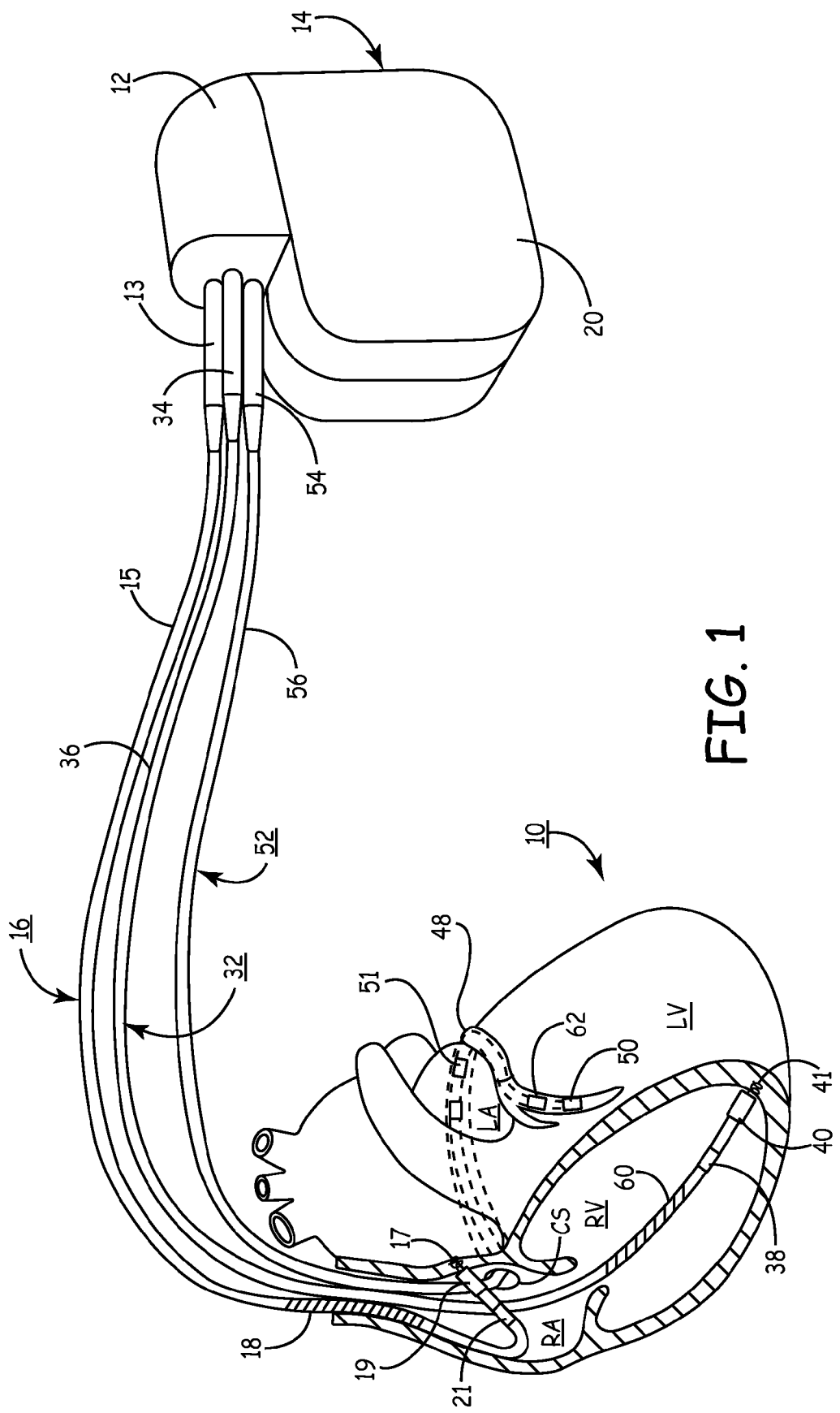
FIG. 1 depicts one embodiment of an ICD implanted relative to a patient's heart.

In the following description, references are made to illustrative embodiments. It is understood that other embodiments may be utilized without departing from the scope of the invention. For purposes of clarity, the same reference numbers are used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

FIG. 1 depicts one embodiment of an ICD 14 implanted relative to a patient's heart 10. ICD 14 is provided for sensing intrinsic heart activity and delivering cardiac stimulation pulses as appropriate to one or more heart chambers. ICD 14 is shown in communication with a patient's heart 10 by way of three leads 16, 32 and 52. The heart 10 is shown in a partially cut-away view illustrating the upper heart chambers, the right atrium (RA) and left atrium (LA), and the lower heart chambers, the right ventricle (RV) and left ventricle (LV), and the coronary sinus (CS) in the right atrium leading into the great cardiac vein 48, which branches to form inferior cardiac veins. Leads 16, 32 and 52 operatively couple ICD 14 with the RA, the RV and the LV, respectively. Each lead has at least one electrical conductor and pace/sense electrode. A remote indifferent can electrode is formed as part of the outer surface of the ICD housing 20. The pace/sense electrodes and the remote indifferent can electrode can be selectively employed to provide a number of unipolar and bipolar pace/sense electrode combinations for pacing and sensing functions.

RA lead 16 is passed through a vein into the RA chamber and may be attached at its distal end to the RA wall using a fixation member 17. RA lead 16 is formed with a connector 13 fitting into a connector bore of ICD connector block 12 for electrically coupling RA tip electrode 19 and RA ring electrode 21 to ICD internal circuitry (not shown) via insulated conductors (not shown) extending within lead body 15. RA tip electrode 19 and RA ring electrode 21 may be used in a bipolar fashion, or in a unipolar fashion with ICD housing 20, for achieving RA stimulation and sensing of RA EGM signals. RA lead 16 is also provided with a coil electrode 18 that may be used for delivering high voltage cardioversion/defibrillation pulses to heart 10 in response to the detection of tachycardia or fibrillation.

RV lead 32 is passed through the RA into the RV where its distal end, carrying RV tip electrode 40 and RV ring electrode 38 provided for stimulation in the RV and sensing of RV EGM signals, may be fixed in or near the RV apex by a distal fixation member 41. RV lead 32 also carries a high-voltage coil electrode 60 for use in cardioverting and defibrillating heart 10. RV lead 32 is formed with a connector 34 fitting into a corresponding connector bore of ICD connector block 12. Connector 34 is coupled to electrically insulated conductors within lead body 36 and connected with distal tip electrode 40, ring electrode 38 and coil electrode 60.

Coronary sinus lead 52 is passed through the RA, into the CS and further into a cardiac vein 48 to extend the distal LV tip electrode 50 and ring electrode 62 alongside the LV chamber to achieve LV stimulation and sensing of LV EGM signals. The LV CS lead 52 is coupled at the proximal end connector 54 into a bore of ICD connector block 12 to provide electrical coupling of conductors extending from electrodes 50 and 62 within lead body 56 to ICD internal circuitry. In some embodiments, LV CS lead 52 could bear a proximal LA pace/sense electrode 51 positioned along CS lead body 56 such that it is disposed proximate the LA for use in stimulating the LA and/or sensing LA EGM signals.

In addition to the transvenous lead-based electrodes shown and the housing 20 acting as an electrode, ICD 14 may be coupled to other electrodes, such as epicardial or subcutaneous electrodes. While a particular ICD system with associated leads and electrodes is illustrated in FIG. 1, numerous implantable cardiac pacemaker and ICD system configurations are possible including one or more leads, which may be transvenous, subcutaneous, or epicardial leads, having various electrode arrangements. Embodiments of the invention may also include subcutaneous pacemaker or ICD systems in which stimulation and sensing electrodes are formed as a part of the device housing and/or carried by subcutaneous leads.

ICD 14 is shown as a multi-chamber device capable of sensing and stimulation in three or all four heart chambers. It is understood that ICD 14 may be modified to operate as a single chamber device for delivering single chamber electrical stimulation therapies (with single chamber or dual chamber sensing) or a dual chamber device for sensing and stimulation in one upper chamber and one lower chamber or both upper or both lower chambers. It is contemplated that embodiments of the present invention may be practiced in a single chamber, dual chamber or multi-chamber implantable cardiac stimulation device. Methods described herein refer generally to "EGM" signals that may be acquired using any intracardiac electrodes. However, as used herein, "EGM signals" or "EGM waveforms" may refer to any cardiac electrical signals acquired by any implanted or external electrodes.

Figure 2:
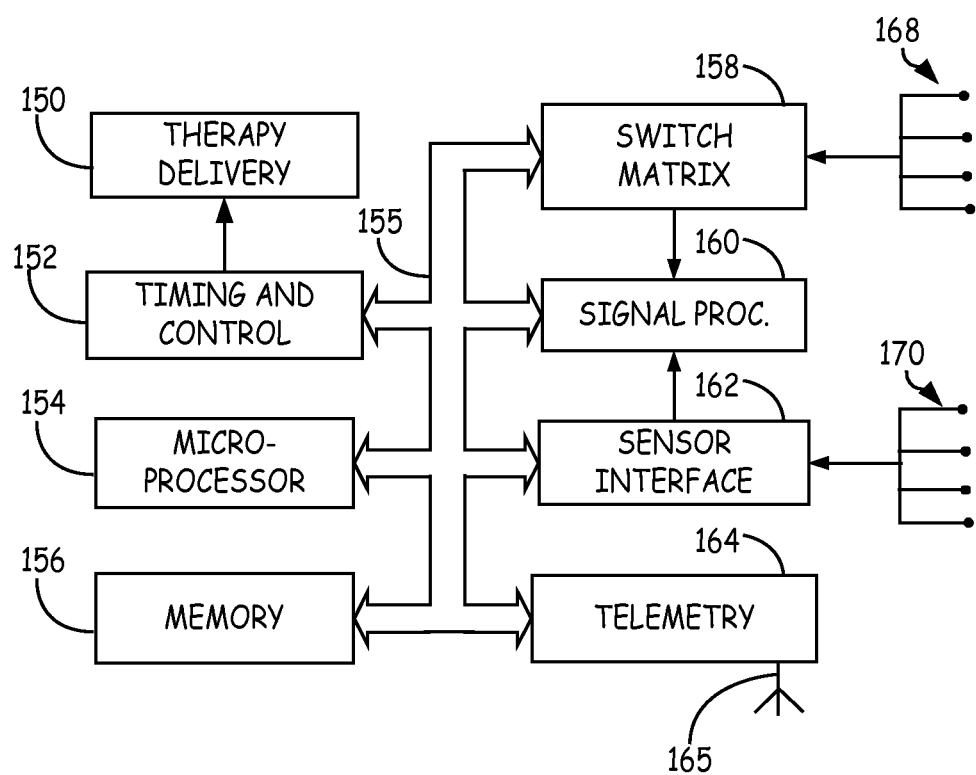
FIG. 2 is a functional block diagram of an implantable cardiac stimulation device such as the ICD shown in FIG. 1.

FIG. 2 is a functional block diagram of an implantable cardiac stimulation device such as the ICD 14 shown in FIG. 1. ICD 14 generally includes timing and control circuitry 152 and an operating system that may employ microprocessor 154 or a digital state machine for timing sensing and therapy delivery functions in accordance with a programmed operating mode. Microprocessor 154 and associated memory 156 are coupled to the various components of IMD 10 via a data/address bus 155. ICD 14 includes therapy delivery unit 150 for delivering electrical stimulation therapies, such as cardiac pacing therapies and arrhythmia therapies including cardioversion/defibrillation shocks, under the control of timing and control 152. Therapy delivery unit 150 is typically coupled to two or more electrodes 168 via an optional switch matrix 158. Switch matrix 158 is used for selecting which electrodes and corresponding polarities are used for delivering electrical stimulation pulses.

Cardiac electrical signals are sensed for determining when an electrical stimulation therapy is needed and in controlling a stimulation mode and the timing of stimulation pulses. Electrodes used for sensing and electrodes used for stimulation may be selected via switch matrix 158. When used for sensing, signals received by electrodes 168 are coupled to signal processing circuitry 160 via switch matrix 158. Signal processor 160 includes sense amplifiers and may include other signal conditioning circuitry and an analog to digital converter. Electrical signals may then be used by microprocessor 154 for detecting physiological events, such as detecting and discriminating cardiac arrhythmias. Signal processing circuitry 160 may include event detection circuitry generally corresponding to R-wave detection circuitry as disclosed in U.S. Pat. No. 5,117,824 (Keimel, et al.), hereby incorporated herein by reference in its entirety.

Arrhythmia detection algorithms may be implemented for detecting ventricular tachycardia (VT), ventricular fibrillation (VF) as well as atrial arrhythmias such as atrial fibrillation (A FIB). Ventricular event intervals (R-R intervals) sensed from the EGM signals are commonly used for detecting ventricular arrhythmias. Additional information obtained such as R-wave morphology, slew rate, other event intervals (P-R intervals) or other sensor signal information may be used in detecting, confirming or discriminating an arrhythmia. Reference is made, for example, to U.S. Pat. No. 5,354,316 (Keimel), U.S. Pat. No. 5,545,186 (Olson et al.) and U.S. Pat. No. 6,393,316 (Gillberg et al.) for examples of arrhythmia detection and discrimination using EGM signals and the provision of arrhythmia therapies in response to arrhythmia detection and discrimination, all of which patents are incorporated herein by reference in their entirety.

In one detection scheme, programmable detection interval ranges designate the range of sensed event intervals indicative of a tachycardia and may be defined separately for detecting slow tachycardia, fast tachycardia and fibrillation. In addition to event interval information, the morphology of the EGM signal may be used in discriminating heart rhythms. According to one embodiment, digitized EGM signals are provided to microprocessor 154 for waveform analysis according to a template matching algorithm as will be described herein. Morphology analysis may be used in conjunction with event interval analysis to improve the sensitivity and specificity of arrhythmia detection methods. Alternatively, the morphology analysis may be used independent of event interval analysis for arrhythmia detection and discrimination.

In response to an arrhythmia detection, a programmed arrhythmia therapy is delivered by therapy delivery module 150 under the control of timing and control 152. A description of high-voltage output circuitry and control of high-voltage shock pulse delivery is provided in the above-incorporated '186 Olson patent.

ICD 14 may additionally be coupled to one or more physiological sensors 170. Physiological sensors 170 may include pressure sensors, accelerometers, flow sensors, blood chemistry sensors, activity sensors or other physiological sensors known for use with implantable cardiac stimulation devices. Physiological sensors may be carried by leads extending from ICD 14 or incorporated in or on the ICD housing.

Signals received at sensor terminals 170 are received by a sensor interface 162 which provides sensor signals to signal processing circuitry 160. Sensor signals are used by microprocessor 154 for detecting physiological events or conditions. For example, ICD 14 may monitor heart wall motion, blood pressure, blood chemistry, respiration, or patient activity or posture. Monitored signals may be used for sensing the need for delivering a therapy under control of the operating system.

The operating system includes associated memory 156 for storing a variety of programmed-in operating mode and parameter values that are used by microprocessor 154. The memory 156 may also be used for storing data compiled from sensed physiological signals and/or relating to device operating history for telemetry out on receipt of a retrieval or interrogation instruction. A waveform morphology classification algorithm may be stored in memory 156 and executed by microprocessor 154 with input received from electrodes 168 for classifying an unknown EGM waveform based on a morphological evaluation as will be described herein.

ICD 14 further includes telemetry circuitry 164 and antenna 165. Programming commands or data are transmitted during uplink or downlink telemetry between ICD telemetry circuitry 164 and external telemetry circuitry included in a programmer or monitoring unit.

Figure 3:
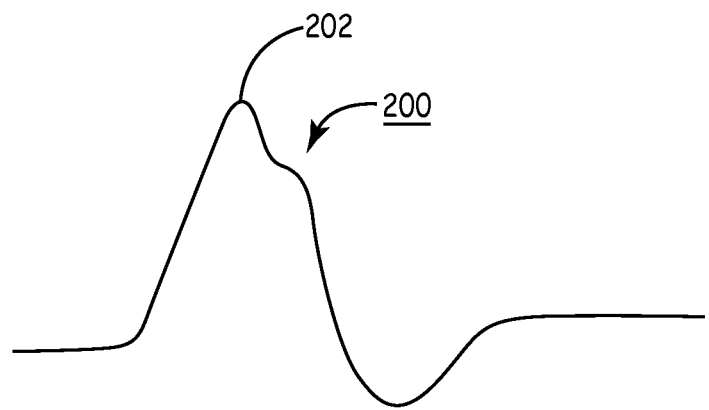
FIG. 3 is an illustration of a known waveform template.

FIG. 3 is an illustration of a known waveform template. The known waveform template 200 is representative of a sinus QRS waveform. A known waveform template may be computed for the P-wave or the QRS complex or any other desired portion of the EGM signal corresponding to any known rhythm, including sinus and non-sinus rhythms. While template 200 is illustrated as a continuous waveform, it is to be understood that template 200 is typically stored as digitized data having a time resolution corresponding to the digital sampling rate.

Template 200 may be generated using any template formulation methods. Examples of methods for generating a template for a known cardiac rhythm are generally described in U.S. Pat. No. 7,062,315 (Koyrakh, et al.) and U.S. Pat. No. 7,242,978 (Cao, et al.), both patents incorporated herein by reference in their entirety.

In general, template 200 is computed using digital analysis of EGM segments acquired during a template acquisition window. A required number of EGM segments meeting predetermined criteria corresponding to a desired heart rhythm are acquired using manual or automated techniques. The acquired EGM segments may be compared by computing cross matches to verify similarity between the acquired segments. EGM segments meeting the required cross matching criteria may then be averaged to compute the known template for the desired heart rhythm. For example, a required number of EGM segments corresponding to the QRS waveform may be acquired for non-paced heart beats that occur at a rate less than a predetermined rate limit to generate a supraventricular tachycardia (SVT) template used to classify fast ventricular rhythms as either SVT or ventricular tachycardia (VT).

A fiducial point 202 of template 200 is identified for use in normalizing the template and/or in time-aligning unknown, sensed EGM waveforms with template 200. For example, the template peak 202 may be identified using a peak-detection algorithm. The amplitude of the peak 202 in A/D converter units may be used to normalize the amplitudes of each of the sample points of the template 200 such that all points fall within an A/D range. In one embodiment, template 200 is defined by 48 sample points acquired at a sampling rate of 256 samples per second. As will be described further below, an unknown EGM waveform may be aligned in time relative to the template 200, to allow morphological evaluation of the unknown EGM signal, by time-aligning the unknown EGM waveform peak with the template peak 202.

While some template comparison methods compare an unknown EGM waveform morphology directly to a generated template, such as template 200, such methods are limited by the quality of the signal. As mentioned previously, clipped and double-peaked waveforms may result in erroneous classifications based on a direct template comparison. FIGS. 4 through 8 illustrate a "blurred" template approach for performing morphological analysis of an unknown waveform. Rather than comparing an unknown waveform directly to the known template, an expected area within which an unknown waveform is expected to fall is defined based on the known template. The unknown waveform is then compared to the boundaries of the expected area. If the unknown waveform falls substantially within the expected area, the unknown waveform can be classified according to the heart rhythm represented by the template.

Figure 4:
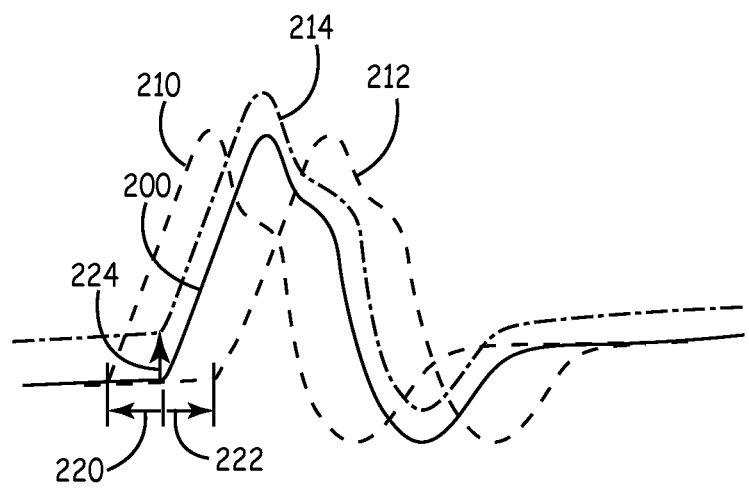
FIG. 4 is an illustration of a template representing a known heart rhythm and three adjusted templates computed from the known template.

FIG. 4 is an illustration of template 200, representing a known heart rhythm, and three adjusted templates 210, 212 and 214 computed from the known template. The adjusted templates 210, 212, and 214 are computed by shifting template 200 in time and/or in amplitude. In the example shown in FIG. 4, adjusted template 210 is computed by shifting template 200 to an earlier time point, referred to herein as a "left" shift. The adjusted template 210 is thus formed by shifting each sample point, or at least a subset of sample points, of template 200 earlier by a predetermined time interval 220. Time interval 220 may correspond to one sampling interval or a multiple of the sampling interval used to generate template 200, or any other predefined time interval. Time interval 220 may be referred to as a shift "width".

Adjusted template 212, is formed by shifting template 200 later in time, also referred to herein as a "right" shift. Adjusted template 212 may be formed by right-shifting template 200 by a time interval 222 that is equal or unequal to time interval 220. In one embodiment, time intervals 220 and 222 are equal and selected to be 4 ms in one embodiment.

Adjusted template 214 is computed by shifting the template 200 in amplitude instead of time. Adjusted template 214 is formed by shifting template 200 to a higher amplitude, also referred to as an "up" shift. Each sample point (or any subset of sample points) of template 200 is shifted up by a shift magnitude 224, also referred to herein as a shift "width". In one embodiment the shift width is 8 A/D units, where one A/D unit corresponds to the resolution of the analog-to-digital converter.

Figure 5:
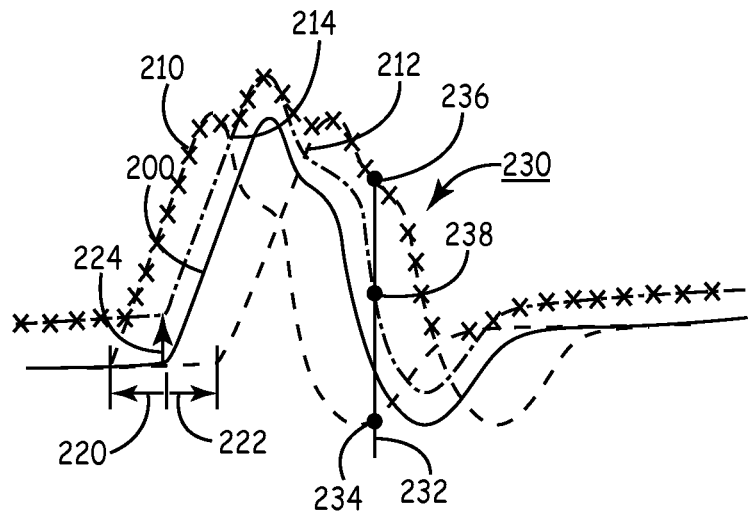
FIG. 5 is a diagram of an upper template boundary computed using the adjusted templates.

FIG. 5 is a diagram of an upper template boundary 230 computed using the adjusted templates 210, 212, and 214. The upper template boundary 230 is indicted by "x's". Each adjusted template 210, 212, and 214 has the same morphology as the original template 200 but that morphology is shifted in time or magnitude. Upper boundary 230 is computed by comparing the amplitude of each of the three adjusted templates 210, 212, and 214 at each time point of template 200. For each time point, the largest amplitude of the adjusted templates 210, 212 and 214 is stored as a point on the upper boundary 230. For example, at time point 232, sample point 234 of adjusted template 210, sample point 236 of adjusted template 212, and sample point 238 of adjusted template 214 are compared. Sample point 236 of the right-shifted template 212 has the highest amplitude and is used as a point defining upper boundary 230.

The upper boundary 230 is thus defined as a composite of points taken from the three adjusted templates 210, 212 and 214. The resulting morphology of boundary 230 is altered from the original morphology of template 200. Upper boundary 230 can be thought of as a boundary of a "blurred template" in that boundary 230 is obtained by "blurring" or shifting template 200 in both time and amplitude.

The upper boundary 230 is limited to the digitized signal range and is therefore limited to the range of the A/D converter units. As such, if a shifted point of any of the adjusted templates 210, 212 and 214 exceeds a maximum A/D converter range, a maximum value within the A/D range is substituted for defining the upper boundary 230. For example 126 A/D units may be used as a maximum value on a scale of 128 A/D units.

Figure 6:
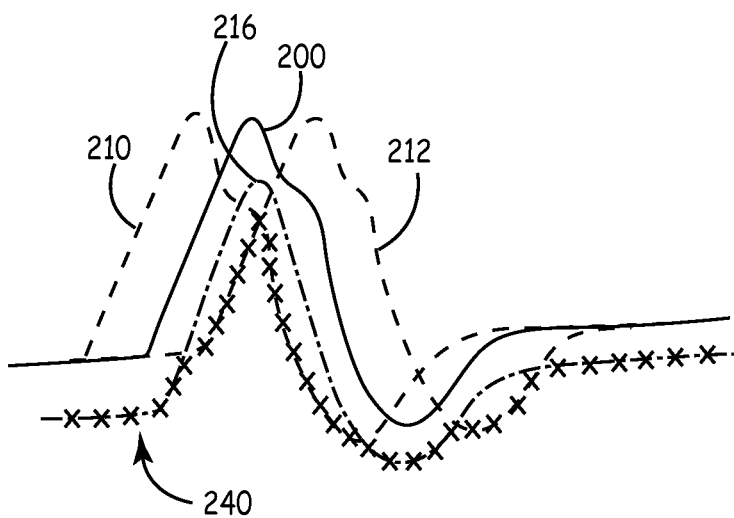
FIG. 6 is a diagram of a lower template boundary computed from a left-shifted adjusted template, right-shifted adjusted template, and a down-shifted adjusted template.

FIG. 6 is a diagram of a lower template boundary 240 computed from left-shifted adjusted template 210, right-shifted adjusted template 212, and a down-shifted adjusted template 216. In this case, in order to compute a lower boundary 240, an adjusted template 216 is computed by shifting original template 200 to a lower amplitude, also referred to as a "down" shift. Each sample point (or a subset of sample points) of template 216 is shifted down in amplitude by a predetermined shift width.

Using the three adjusted templates 210, 212 and 216, the lower template boundary 240, indicated by the "x" symbols, is computed in a similar manner as described above. Instead of choosing the highest amplitude sample point of each of the three adjusted templates 210, 212, and 216, however, the lowest amplitude of the adjusted templates at a given time point is selected for use in defining lower boundary 240. Like upper boundary 230, lower boundary 240 has an altered morphology compared to the original morphology of template 200. The lower boundary 240 is also limited to be defined within the range of the A/D converter units.

Figure 7:
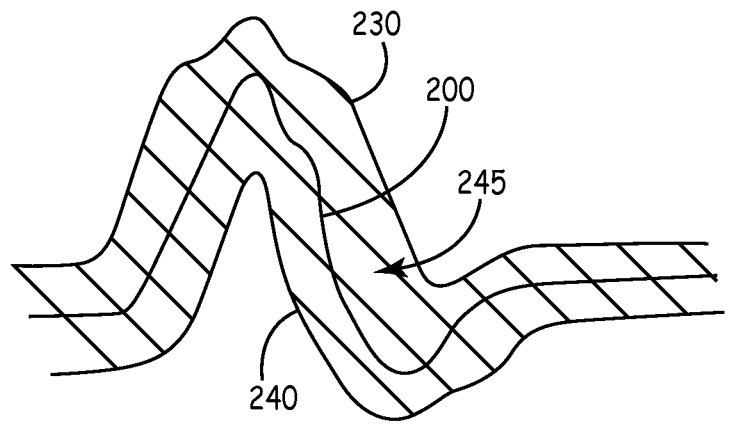
FIG. 7 is a diagram of the upper and lower boundaries defining a "blurred template" for use in classifying unknown cardiac EGM waveforms.

FIG. 7 is a diagram of the upper and lower boundaries 230 and 240 defining a "blurred template" for use in classifying unknown cardiac waveforms. The "blurred template"

bounded by the upper and lower boundaries 230 and 240 defines an expected morphology area 245. The original template 200 is shown relative to upper boundary 230, computed as described in conjunction with FIG. 5, and lower boundary 240, computed as described in conjunction with FIG. 6. A digitized unknown EGM waveform is compared to the upper and lower boundaries 230 and 240 as opposed to comparing directly to original template 200.

While one specific method for computing upper and lower boundaries 230 and 240 has been described, it is recognized that numerous variations may be conceived for computing the upper and lower boundaries as a complex of any combination of points selected from any number of adjusted templates formed by shifting the original template 200 in time and/or amplitude. Upper and lower boundaries may also include points corresponding to the original unshifted template 200 in some embodiments.

Figure 8:
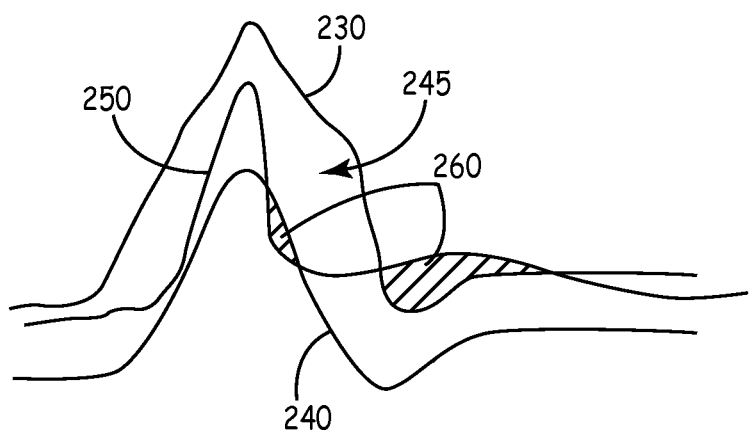
FIG. 8 is a diagram of an unknown QRS waveform time-aligned with the original template (not shown for the sake of clarity) for comparison to upper and lower boundaries.

FIG. 8 is a diagram of an unknown QRS waveform 250 time-aligned with the original template (not shown for the sake of clarity) for comparison to upper and lower boundaries 230 and 240. As will be described below, the unknown QRS waveform 250 is time-aligned with the original known template by aligning selected fiducial points or features of the waveforms in time. Rather than comparing sample point values of the unknown waveform directly to the known template, however, the unknown waveform 250 is compared to the upper and lower boundaries 230 and 240.

Points falling outside the expected area 245 represent a deviation from the expected morphology. As will be described in greater detail below, the distances from unknown EGM waveform sample points falling outside the expected area 245 to the nearest boundary 230 or 240 are computed and used to estimate an error area 260. The error area 260 represents the area of the unknown waveform 250 falling outside the expected morphology area 245 defined by upper and lower boundaries 230 and 240. The estimated error area 260 is used to compute a match metric used for determining if the unknown waveform 250 matches the original known template 200 and can thus be classified accordingly.

Figure 9:
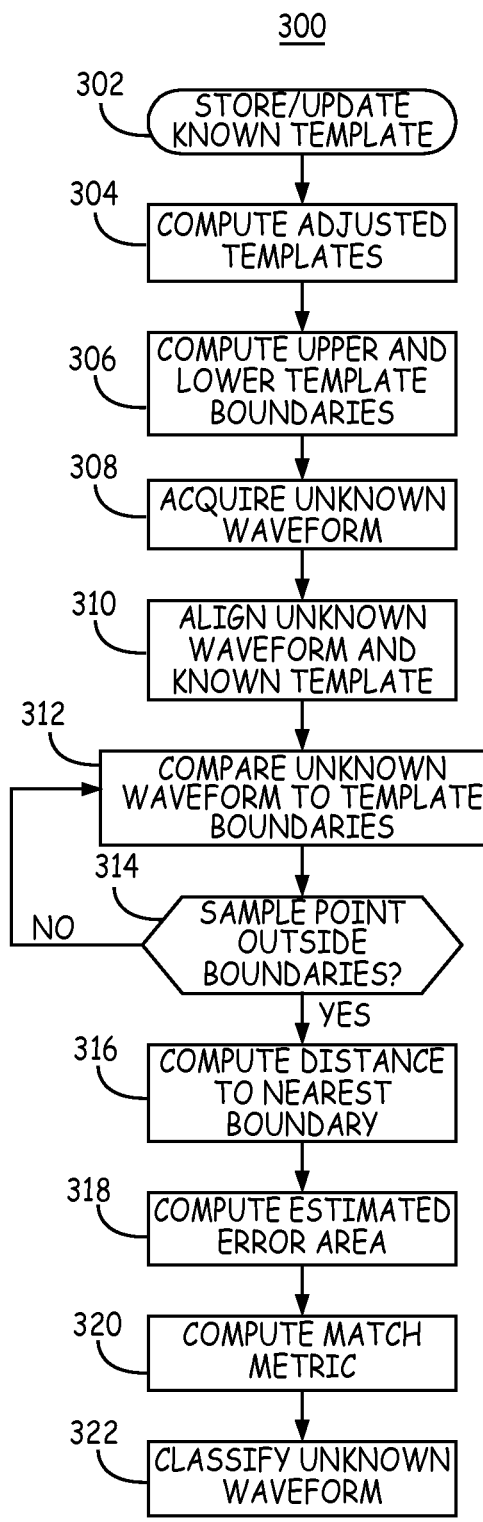
FIG. 9 is a flow chart of a method for classifying an EGM waveform using a blurred template comparison.

FIG. 9 is a flow chart of a method for classifying an EGM waveform using a blurred template comparison. Flow chart 300 is intended to illustrate the functional operation of the device, and should not be construed as reflective of a specific form of software or hardware necessary to practice the methods described. It is believed that the particular form of software, firmware and/or hardware will be determined primarily by the particular system architecture employed in the device and by the particular detection and therapy delivery methodologies employed by the device. Providing software and hardware to accomplish the described functionality in the context of any modern ICD, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 302 an EGM template representing a known cardiac rhythm is generated and stored. For example, as described earlier, a stored template may be generated from acquired normal ventricular beats (non-paced and below a predetermined heart rate limit) to represent an SVT template used to classify fast ventricular beats as SVT or VT beats. It is recognized that template generation and storing performed at block 302 may include generating a template for the first time after implanting an ICD in a patient as well as performing template updates based on ongoing template quality monitoring as generally described in the above-incorporated Koyrakh '315 patent. Method 300 is not limited to any particular template generation and updating methods. The original known template may be generated and updated using any known methods.

Furthermore, it is recognized that one or more templates may be generated and stored at block 302. Multiple templates may be stored for different known cardiac rhythms, e.g. SVT, VT, normal sinus rhythm, etc. and/or different sensing electrode configurations, e.g., true bipolar, unipolar, integrated bipolar, etc. The "blurred template" approach described herein for comparing an acquired unknown EGM waveform to a known template may be applied to any type of template and may be used to make multiple comparisons of an unknown waveform to multiple templates for classifying the unknown waveform.

At block 304, adjusted templates are computed by shifting the known template stored at block 302 in time and/or amplitude as described above. At block 306, upper and lower template boundaries are computed using the adjusted templates (and optionally the original template) as described previously for defining a "blurred template", bounded by the upper and lower boundaries which define an expected morphology area for a given cardiac event type. It is recognized that the adjusted templates and template boundaries computed at blocks 304 and 306 can be computed for an original stored template and updated each time the stored template is updated.

At block 308, an EGM waveform for an unknown cardiac rhythm is acquired by sensing the EGM signal during a desired sensing window and sampling the signal to obtain a digitized EGM waveform. A fiducial point is then identified on the unknown waveform and the unknown waveform sample point amplitudes are normalized in the range of A/D converter units using the fiducial point amplitude in the same manner used to normalize the known template as described above in conjunction with FIG. 3. In one embodiment, the R-wave peak amplitude is used to normalize the sample point amplitudes.

The unknown waveform and the known template are aligned in time at block 310. The time alignment is performed by identifying a fiducial point of the known template, for example the R-wave peak, and a corresponding fiducial point on the unknown waveform. The corresponding fiducial points are then aligned in time to superimpose the unknown waveform over the known template in time. Other fiducial points that may be used for time alignment include, but are not limited to, any maximum or minimum peak, a zero-crossing or an inflection point.

At block 312, the unknown waveform sample points are each compared to the upper and lower template boundaries. If the unknown waveform at a given time point is less than or equal to the upper boundary and greater than or equal to the lower boundary, the sample point is determined to fall within the expected morphology area. Method 300 returns to block 312 to analyze the next unknown waveform sample point to the upper and lower boundaries.

If the unknown waveform sample point exceeds the upper boundary or falls below the lower boundary at any give time point as determined at block 314, i.e. the sample point falls outside the expected morphology area defined by the upper and lower boundaries, the distance from the nearest boundary is computed at block 316. Block 316 is performed for each unknown waveform sample point falling outside the upper and lower template boundaries. Methods for computing the distance between a sample point and the nearest boundary will be described below. In alternative embodiments, the distance between the sample point falling outside the expected area and the original template may be computed.

Once all of the unknown waveform sample points have been examined, an estimated error area is computed at block 318. In one embodiment, the estimated error area is calculated using the distances computed at block 316 with each distance assigned a weighting. The unknown waveform sample points falling within the upper and lower boundaries are ignored for purposes of computing the error area. Those distances can be considered to be assigned a zero weighting. Sample points falling within a predetermined distance threshold from the nearest upper or lower boundary may be assigned a weighting of "1". Sample points falling greater than the predetermined distance threshold from the nearest upper or lower boundary may be assigned a weighting of greater than one, for example a weighting of 2 or 4.

The predetermined distance threshold used for assigning weights may be defined as the "shift width" applied when shifting the original template to form the adjusted templates. In one embodiment, the shift width is 8 A/D converter units. If a sample point is within the shift width of an upper or lower boundary, the distance computed for the point is assigned a weighting factor of 1 and summed with the other weighted distances to compute the estimated error area.

If a sample point is more than one shift width of the upper or lower boundary, the distance computed for that point is multiplied by the assigned weighting factor, for example 2 or 4, and the weighted distance is summed with the other weighted distances to compute the estimated error area. It is recognized that various embodiments can include other weighting factors than the examples given here, each weighting assigned according to various predetermined distance thresholds or ranges from the upper and lower boundaries. More than one distance threshold may be used, i.e. more than the two distance ranges described herein (less than one shift width and greater than one shift width from the nearest boundary).

A match metric is computed at block 320 using the estimated error area and optionally other comparison measurements made between the unknown waveform and the blurred template and/or the original template. In one embodiment, the match metric is computed using a ratio of the estimated error area to the total number of sample points. The match metric may be computed as:

Match metric=100−(EEA/sample#)*$C$ where "EEA" is the estimated error area computed at block 318, "sample #" is the number of sample points in the digitized waveform, and "C" is a coefficient that may be assigned a value based on test outcomes of the classification method 300. Depending on the template and waveform acquisition methods used, the sample number may be a constant or variable. In one embodiment 48 sample points are used.

The match metric will be inversely correlated to the estimated error area in that the higher the error area the lower the match metric. Other terms may be used in combination with the estimated error area in computing a match metric. For example, in one embodiment, the match metric may be computed as a function of the estimated error area and a ratio of the template peak amplitude and the unknown waveform peak amplitude. As such, a match metric may be computed using comparisons between the unknown waveform and both the original known template and the upper and lower boundaries computed from the original template.

At block 322 the match metric is used to classify the unknown waveform. For example, the match metric may be compared to a classification threshold at block 322. If the match metric exceeds a match threshold, the unknown waveform is classified as the cardiac event represented by the known template. If the match metric is less than the match threshold, the unknown waveform may be classified as a different event than the template or compared to additional known templates for classifying the unknown beat.

In one embodiment, a known template stored at block 302 corresponds to an SVT template generated from intrinsically conducted QRS waveforms occurring at a heart rate below a predetermined rate limit. Method 300 is invoked when a fast ventricular rate is detected, for example when ventricular tachycardia detection criteria based on RR intervals are satisfied. A QRS waveform acquired during this unknown fast rhythm is compared to the upper and lower template boundaries to determine if the waveform matches the "blurred" template. If the QRS waveform matches the "blurred" template, the QRS waveform is classified as an SVT beat. If the QRS waveform does not match the template, the QRS waveform is classified as a VT beat, i.e. originating in the ventricles as opposed to originating in the atria. Additional rhythm classification criteria may then be applied to classify the unknown fast ventricular rhythm as SVT or VT based on the number of beats classified as SVT and VT (and other beat classifications if available). Accurate classification of the unknown beats occurring during a fast ventricular rhythm allows SVT to be properly distinguished from VT, allowing appropriate therapeutic action to be taken.

Figure 10:
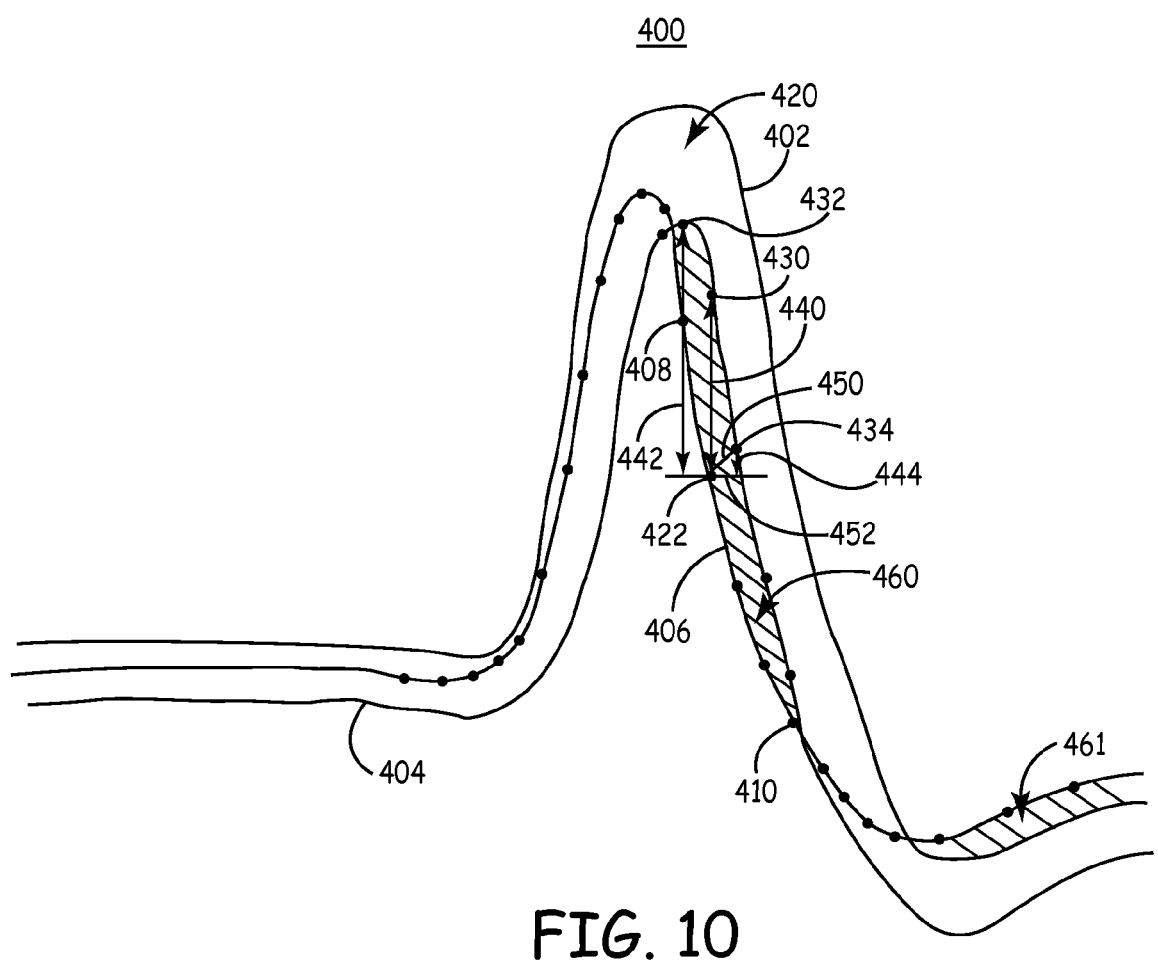
FIG. 10 is a diagram of one method for computing a distance between a waveform sample point and the nearest boundary for use in computing a template match metric.

FIG. 10 is a diagram 400 of one method for computing a distance between a waveform sample point and the nearest boundary for use in computing a template match metric. In FIG. 10, an upper boundary 402, a lower boundary 404, and an unknown QRS waveform 406 are shown. The unknown QRS waveform 406 has been time-aligned with the original template (not shown) used to compute the upper and lower template boundaries 402 and 404. Sample points 408 and 410 of QRS waveform 406, and each sample point therebetween, are seen to fall outside the expected morphology area 420, defined by upper and lower boundaries 402 and 404.

In one embodiment, a distance between a sample point falling outside the expected morphology area 420 could be computed as the difference between the sample point amplitude and the amplitude of the nearest boundary at the same time point. For example, the difference 440 between sample point 422 on the unknown waveform 406 and point 430 on the lower boundary 404 may be computed as the distance from point 422 to the lower boundary 404. This distance 440 may then be used in computing an estimate of the error area 460. In a similar manner, other distances can be computed as the difference in amplitude at a given time point between lower boundary 404 and the respective sample points between and including points 408 and 410, which all fall below lower boundary 404. These distances computed as an amplitude difference between an unknown sample point and the nearest boundary may then be summed to estimate the error area 460.

Another method for computing a distance between a sample point falling outside the expected morphology area 420 and the nearest upper or lower boundary 402 and 404 is illustrated using sample point 422. This alternative method is used to estimate the actual shortest distance between the unknown waveform sample point 420 and the nearest boundary 402 or 404. The estimated actual shortest distance may provide a more accurate representation of the deviation of the morphology of the unknown waveform from the blurred template than a distance computed as the difference between the sample point 420 and a simultaneously occurring sample point on one of boundaries 402 and 404.

First, the absolute values of amplitude differences between sample point 422 and the amplitudes of multiple selected lower boundary points are determined. In one embodiment three sample point amplitude differences are computed. One difference 440 is computed between sample point 422 and lower boundary sample point 430 occurring at the same time as sample point 422. A second amplitude difference 442 is computed between the sample point 422 and lower boundary point 432 occurring one time point (one sampling time interval) earlier than sample point 422. A third difference 444 is computed between sample point 422 and lower boundary point 434 occurring one sampling time interval later than sample point 422.

In one embodiment, the smallest of the computed differences 440, 442 and 444, in this example difference 444, is selected to compute an estimated distance 450 between the sample point 422 and the lower boundary 404. The distance, D, 450 from sample point 422 to lower boundary 404 may be estimated as the length of the hypotenuse of a right triangle according to the Pythagorean theorem:

$$D^2 = a^2 + b^2$$

wherein a is the amplitude difference 444 and b is the sampling time interval 452 between points 422 and 434.

Alternatively, a simplified distance metric may be applied as:

$$D = a + x$$

wherein "a" is the smallest amplitude difference between the sample point and the selected nearest boundary points and x is the square root of the time interval between the sample point and the smallest amplitude difference boundary point. In the example shown, "a" is difference 444 and "x" is the square root of the sample time interval, which may be 8 A/D units in one embodiment in which case x is the square root of 8 which may be rounded up to an integer value of 3. If the smallest amplitude difference were to be difference 440, that is the boundary point occurring at the same time as the sample point, "x" would be 0 and the distance would simply equal the amplitude difference between the sample point and the nearest boundary point.

The estimated error area 460, i.e. the area bounded by the unknown QRS waveform and the nearest boundary 402, outside the expected area 450, is computed using the estimated distance 450. As described previously, the distance 450 is multiplied by a weighting coefficient based on the magnitude of distance 450. For example if the computed distance 450 is greater than a shift width used to compute an adjusted template as described previously, the distance may be multiplied by a weighting coefficient greater than one, for example a weighting of 2 or 4. If the computed distance 450 is less than the shift width, the distance may be multiplied by a weighting coefficient of one.

The weighted distance 450 is then summed with the weighted distances computed for sample points 408 and 410 and each sample point there between falling outside the expected morphology area 420 and defining error area 460 between QRS waveform 406 and lower boundary 404. The estimated error area is then used to compute a match metric as described previously.

While specific methods for computing an estimate of error area 460 are described, it is recognized that numerous computational methods may be implemented for estimating the error area 460, which may include alternative methods for estimating the distance between unknown QRS waveform sample points and the upper and lower boundaries of an expected morphology area. For example, various integration or other discrete computational methods may be used to estimate error area 460. Such methods may include estimating a difference between an area under a nearest boundary and an area under the QRS waveform between a time point of a first sample point falling above/below the respective boundary and a last time point of a sample point falling above/below the respective boundary.

An unknown QRS waveform 406 may have interrupted segments falling outside the expected area 420, separated by segments falling within the expected area 420. As such, multiple portions 460 and 461 of a total error area falling outside expected area 420 may be computed separately then summed together to compute the total estimated error area.

Figure 11:
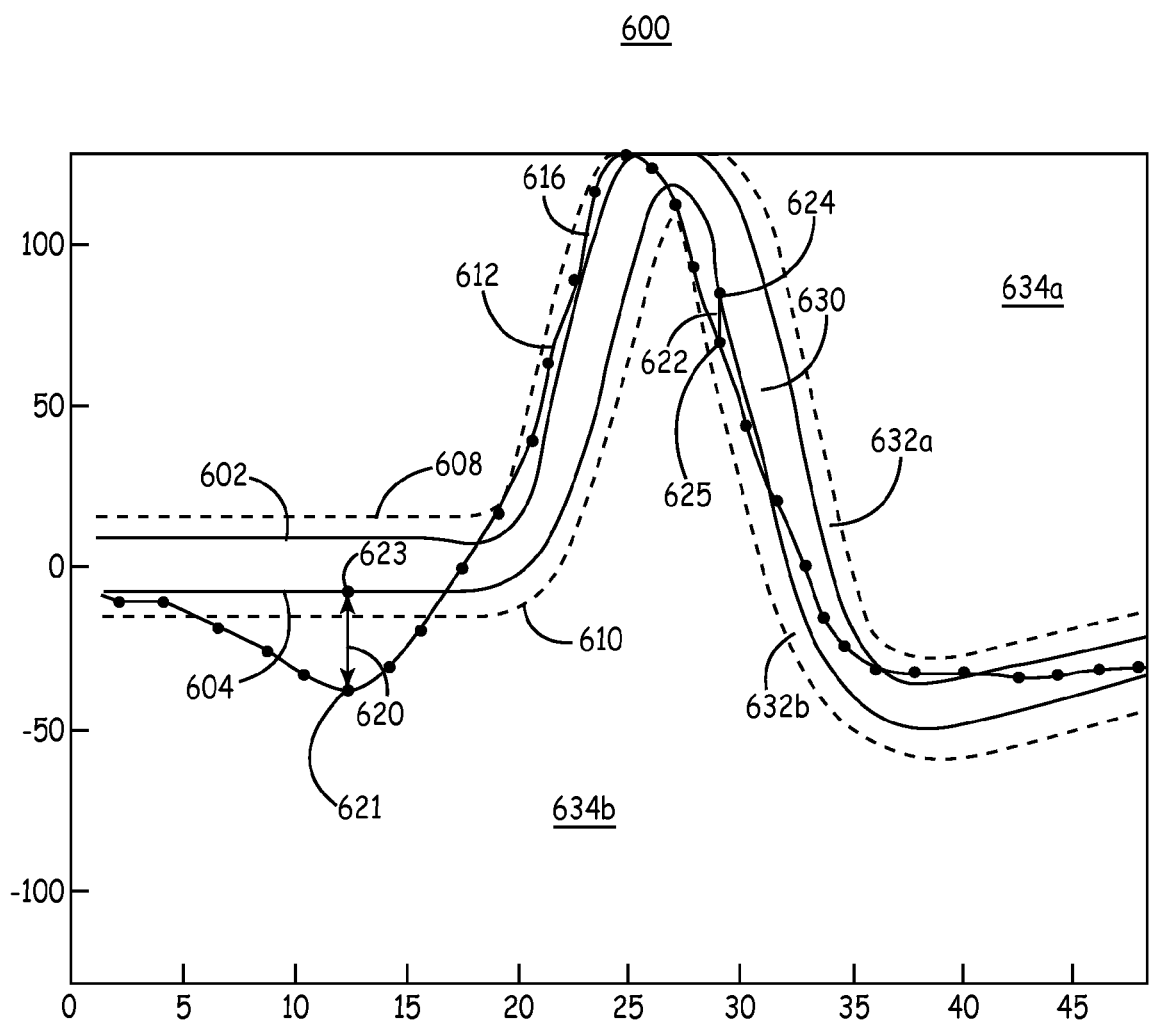
FIG. 11 is a diagram 600 of another method for computing an error area for use in computing a template match metric for an unknown QRS waveform.

FIG. 11 is a diagram 600 of another method for computing an error area for use in computing a template match metric for an unknown QRS waveform. An expected morphology area 630 is bounded by an upper boundary 602 and a lower boundary 604. Upper and lower boundaries 602 and 604 may be computed as generally described above using a known template (not shown for the sake of clarity). In addition to computing the upper and lower boundaries, an outer upper boundary 608 and an outer lower boundary 610 are computed.

The outer boundaries 608 and 610 may be computed using any combination of the original known template and the upper and lower boundaries 602 and 604 shifted in time and/or amplitude. In one embodiment, the outer upper boundary 608 is computed using the original template left-shifted and right shifted and the upper boundary shifted upward, e.g., by 8 A/D units. The maximum amplitude of the left-shifted template, the right-shifted template, and the up-shifted upper boundary at a given sample time point is used to define the outer upper boundary 608. The template may be shifted to the left and to the right a larger time interval width than the time interval used to compute time-shifted templates for deriving upper boundary 602. For example, the upper boundary 602 may be computed using the original known template left-shifted and right-shifted in time by one sample time interval, e.g., 4 ms. The outer upper boundary may be computed using the original template left-shifted and right-shifted in time by two sample time intervals, e.g. 8 ms.

Similarly the outer lower boundary 610 can be computed using the original template left-shifted and right-shifted and the lower boundary shifted downward. The lowest amplitude of the three shifted waveforms at each sample point is selected to define the outer lower boundary 610.

The areas 632a and 632b, referred to collectively as 632, occurring between The upper boundary 602 and outer upper boundary 608 define an area 632a. The lower boundary 604 and outer lower boundary 610 define an area 632b. The areas 632a and 632b are referred to collectively as an inner error zone 632.

An area 634a occurs outside outer upper boundary 608. An area 634b occurs outside outer lower boundary 610. The areas 634a and 634b are referred to collectively as an outer error zone 634. The inner and outer error zones 632 and 634 are used to determine the weighting of a distance calculated between an unknown waveform 612 and the nearest of the upper and lower boundaries 602 and 604, respectively.

In one embodiment, a distance 620 is computed as the difference between a sample point 621 of unknown waveform 612 and the corresponding sample point 623 of lower boundary 604, occurring at the same sample time point. Since sample point 621 falls outside the outer lower boundary 610, i.e., in outer error zone 634, the distance 620 is multiplied by a weighting factor, e.g. a weighting of 4, before being summed with other distances for computing an error area.

Sample point 625 falls between lower boundary 604 and outer lower boundary 610 within the inner error zone 632. A corresponding distance 622 from lower boundary 604 may be computed as the difference between unknown waveform sample point 625 and the corresponding lower boundary sample point 624. Since sample point 625 falls within the inner error zone 632, a lower weighting factor, for example a weighting factor of 1, may be applied to distance 622 before summing distance 622 with other computed distances for computing an error area.

Thus, in alternative embodiments, a straight-forward distance calculation may be made by computing the difference between an unknown sample point and a corresponding upper or lower boundary sample point. Weighting factors may be applied to the computed distances based on the location of the unknown waveform sample point relative to the outer boundaries 608 and 610, rather than based on a threshold comparison as generally described above in conjunction with FIG. 10.

While only one set of outer boundaries 608 and 610 are shown in FIG. 11, it is contemplated that multiple outer boundaries may be computed using any combination of time- and/or amplitude shifted templates and/or shifted inner boundaries to define one or more intermediate error zones between an inner error zone and an outer error zone. Each intermediate error zone would be assigned a weighting factor intermediate the adjacent error zones. Distances from the upper and lower boundaries for unknown waveform sample points falling within intermediate error zones would be multiplied by corresponding intermediate weighting factors before being summed with other distances for computing an error area.

Figure 12:
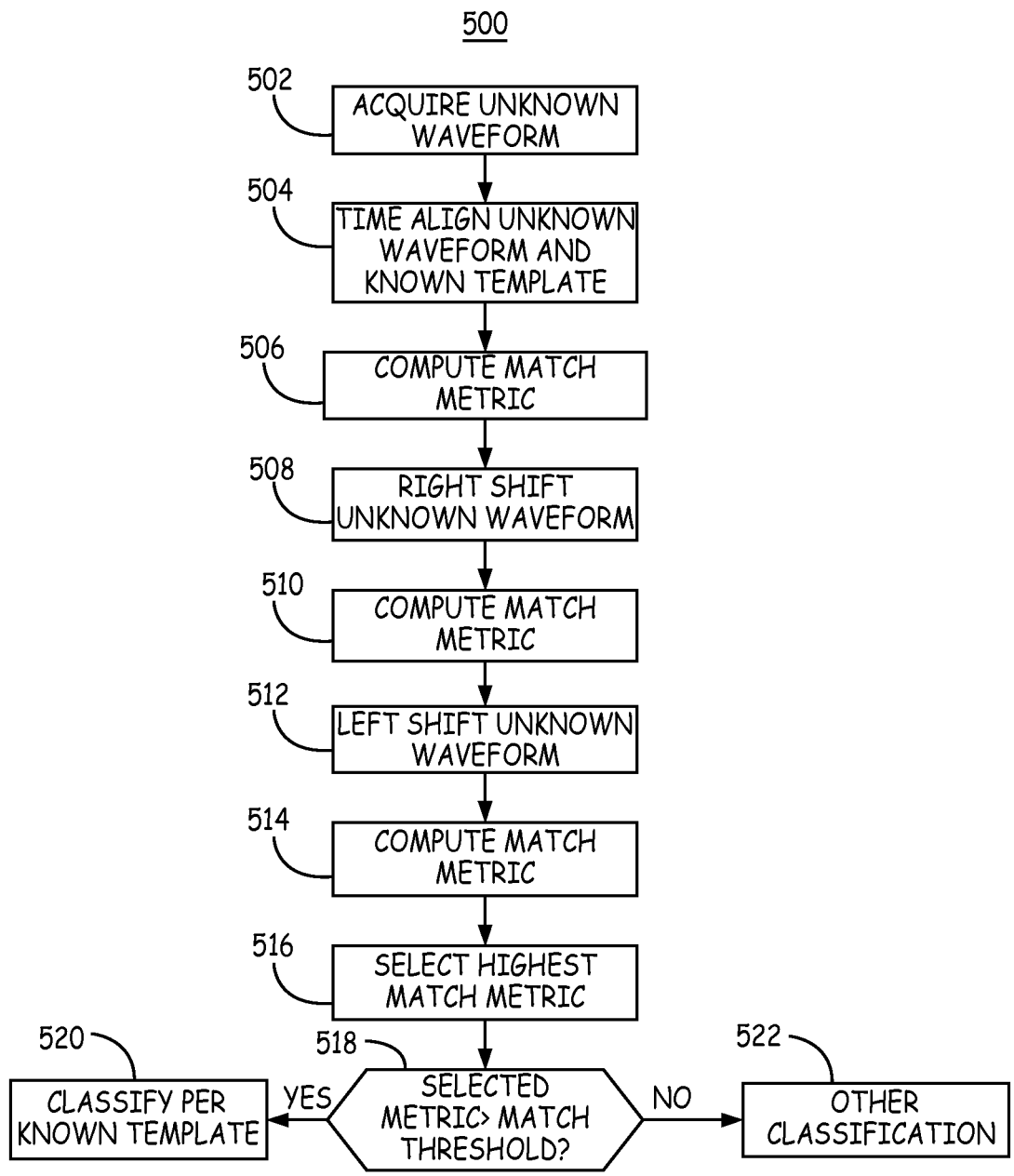
FIG. 12 is a flow chart of an alternative method for computing a match metric using a "blurred" template approach.

FIG. 12 is a flow chart of an alternative method 500 for computing a match metric using a "blurred" template approach. At block 502, an unknown waveform is acquired. At block 504, the unknown waveform is aligned in time with a previously determined known template. A match metric is computed at block 506, as generally described above in conjunction with FIG. 9, by estimating an error area corresponding to the areas of the unknown waveform falling outside an expected morphology area defined by upper and lower template boundaries.

At block 508, the unknown waveform is shifted in time relative to the known template. For example, the unknown waveform that had been aligned in time with the known template may be right shifted by one sample time interval. In other words, each sample point of the time-aligned unknown waveform would be shifted right one time interval. A new match metric is computed at block 510 for the right-shifted unknown waveform using the same upper and lower template boundaries used at block 506.

The unknown waveform is then left-shifted at block 512 relative to the known template, and a new match metric is computed for the left-shifted unknown waveform at block 514, again using the same upper and lower template boundaries as used at blocks 506 and 510.

At block 516, the highest of the match metrics computed for the time-aligned, right-shifted, and left-shifted unknown waveform is selected for use in classifying the unknown waveform. At block 518, the selected metric is compared to a match threshold. If the selected metric exceeds the threshold, the unknown waveform is classified according to the known template type at block 520.

If the selected metric does not exceed the match threshold, the unknown waveform is classified as being different than the known template at block 522. For example, during a fast ventricular rate, morphology analysis of the unknown EGM may be used to discriminate the fast rate as SVT or VT. A match at block 518 would result in the unknown beat being classified as an SVT beat at block 520. A non-match at block 518 could result in the unknown waveform being classified as a VT beat at block 522. Arrhythmia detection algorithms may then detect the ongoing rhythm as SVT or VT depending on the number of beats classified as SVT beats and the number of beats classified as something other than SVT beats, e.g. VT beats.

Method 500 illustrates a template comparison method that utilizes right-shifted and left-shifted, i.e. time-shifted, unknown waveforms for computing multiple match metrics for a given unknown waveform. It is recognized that an unknown waveform may be adjusted by shifting the waveform in any increments of time and/or amplitude for computing multiple match metrics. Furthermore, a computed match metric may combine measures computed from comparisons between the template boundaries and any of the non-adjusted unknown waveform and the adjusted unknown waveforms. In other words an equation used to compute a match metric may include terms computed using the time-aligned unknown waveform, one or more time-shifted unknown waveforms, one or more amplitude-shifted unknown waveforms, or any combination thereof. The highest match metric among different shifts of the unknown waveform may be used as the representative match for the beat. The match metric is sensitive to shifting of the unknown waveform relative to the original template because the selected fiducial point for aligning the unknown waveform and original template may not optimally align the waveform with the template.

Thus, an implantable medical device and associated methods for performing EGM morphology analysis for use in classifying cardiac signals and detecting and discriminating cardiac arrhythmias have been presented in the foregoing description with reference to specific embodiments. It is appreciated that various modifications to the referenced embodiments may be made without departing from the scope of the invention as set forth in the following claims.

The invention claimed is:

1. A method for use in an implantable medical device, comprising:
sensing a cardiac signal;
deriving a known template representing a known waveform morphology from the cardiac signal;
computing one or more adjusted templates, each of the one or more adjusted templates computed by shifting the known template in at least one of time and amplitude;
computing an upper boundary using the one or more adjusted templates;
computing a lower boundary using the one or more adjusted templates, wherein an area is defined between the upper and lower boundaries;
acquiring an unknown waveform morphology from the cardiac signal;
comparing the unknown waveform morphology to the upper and lower boundaries; and
classifying the unknown waveform morphology based on the comparison.

2. The method of claim 1 wherein the upper boundary and the lower boundary are each offset from the known template.

3. The method of claim 2 wherein computing the upper boundary comprises
selecting a highest amplitude of the one or more adjusted templates at each of a plurality of time points and defining the upper boundary using the selected highest amplitudes, and wherein computing the lower boundary comprises selecting a lowest amplitude of the one or more adjusted templates at each of the plurality of time points and defining the lower boundary using the selected lowest amplitudes.

4. The method of claim 1 wherein comparing the unknown waveform to the upper and lower boundaries comprises
computing an estimated area of the unknown waveform falling outside the area defined by the upper boundary and the lower boundary.

5. The method of claim 4 wherein computing the estimated area comprises identifying a sample point of the unknown waveform falling outside the area defined by the upper and lower boundaries and computing a distance of the identified sample point from a nearest one of the upper boundary and the lower boundary.

6. The method of claim 5 wherein computing the distance comprises determining a smallest amplitude difference between the identified sample point and a plurality of sample points along the nearest one of the upper and lower boundaries.

7. The method of claim 5 wherein computing the estimated area comprises multiplying the distance by a weighting factor and summing the distance with other distances computed using other identified sample points of the unknown waveform falling outside the upper and lower boundaries.

8. The method of claim 7 further comprising:
computing an outer upper boundary that is offset from the upper boundary, wherein a first region is defined between the outer upper boundary and the upper boundary;
computing an outer lower boundary that is offset from the lower boundary, wherein a second region is defined between the outer lower boundary and the lower boundary; and
determining the weighting factor based on the location of the identified sample point relative to the outer upper boundary and the outer lower boundary.

9. The method of claim 8 wherein computing the outer upper boundary comprises shifting the upper boundary in one of time and amplitude, and wherein computing the outer lower boundary comprises shifting the lower boundary in one of time and amplitude.

10. The method of claim 5 further comprising:
determining an adjusted unknown waveform by shifting the unknown waveform in time relative to the known template;
computing an adjusted estimated area of the adjusted unknown waveform falling outside the area defined by the upper and lower boundaries; and
classifying the unknown waveform using the lowest one of the estimated area and the adjusted estimated area.

11. The method of claim 1 wherein at least one of the upper and lower boundaries includes a portion of the known template.

12. The method of claim 2 wherein at least a portion of the known template is included in the area between the upper and lower boundaries.

13. The method of claim 4 further comprising, prior to computing the estimated area, aligning in time a selected point of the unknown waveform with a corresponding selected point of the known template.

14. An implantable medical device, comprising;
electrodes for sensing a cardiac signal;
memory for storing a known template representing a known waveform morphology of the cardiac signal;
a processor coupled to the memory, the processor configured to:
receive the cardiac signal;
compute one or more adjusted templates, each of the one or more adjusted templates computed by shifting the known template in at least one of time and amplitude;
compute an upper boundary using the one or more adjusted templates;
compute a lower boundary using the one or more adjusted templates, wherein an area is defined between the upper and lower boundaries;
acquire an unknown waveform morphology from the cardiac signal;
compare the unknown waveform morphology to the upper and lower boundaries; and
classify the unknown waveform morphology based on the comparison.

15. The device of claim 14 wherein the upper boundary and the lower boundary are each offset from the known template.

16. The device of claim 15 wherein the processor is configured to compute the upper boundary
by selecting a highest amplitude of the one or more adjusted templates at each of a plurality of time points and
defining the upper boundary using the selected highest amplitudes, and wherein the processor is configured to compute the lower boundary by selecting a lowest amplitude of the one or more adjusted templates at each of the plurality of time points and defining the lower boundary using the selected lowest amplitudes.

17. The device of claim 14 wherein the processor is configured to compare the unknown waveform to the upper and lower boundaries
by computing an estimated area of the unknown waveform falling outside the area defined by the upper boundary and the lower boundary.

18. The device of claim 17 wherein the processor is configured to compute the estimated area by identifying a sample point of the unknown waveform falling outside the area defined by the upper and lower boundaries and computing a distance of the identified sample point from a nearest one of the upper boundary and the lower boundary.

19. The device of claim 18 wherein the processor is configured to compute the distance by determining a smallest amplitude difference between the identified sample point and a plurality of sample points along the nearest one of the upper and lower boundaries.

20. The device of claim 18 wherein the processor is configured to compute the estimated area by multiplying the distance by a weighting factor and summing the distance with other distances computed using other identified sample points of the unknown waveform falling outside the upper and lower boundaries.

21. The device of claim 20 wherein the processor is configured to compute the estimated area by:
computing an outer upper boundary that is offset from the upper boundary, wherein a first region is defined between the outer upper boundary and the upper boundary;
computing an outer lower boundary that is offset from the lower boundary, wherein a second region is defined between the outer lower boundary and the lower boundary; and
determining the weighting factor based on the location of the identified sample point relative to the outer upper boundary and the outer lower boundary.

22. The device of claim 21 wherein the processor is configured to compute the outer upper boundary by shifting the upper boundary in one of time and amplitude, and wherein the processor is configured to compute the outer lower boundary by shifting the lower boundary in one of time and amplitude.

23. The device of claim 17 wherein the processor is configured to compare the unknown waveform to the upper and lower boundaries by:

determining an adjusted unknown waveform by shifting the unknown waveform in time relative to the known template;

computing an adjusted estimated area of the adjusted unknown waveform falling outside the area defined by the upper and lower boundaries; and classifying the unknown waveform using the lowest one of the estimated area and the adjusted estimated area.

24. The device of claim 14 wherein at least one of the upper and lower boundaries includes a portion of the known template.

25. The device of claim 15 wherein at least a portion of the known template is included in the area between the upper and lower boundaries.

26. The device of claim 17 wherein the processor is configured to align, in time, a selected point of the unknown waveform with a corresponding selected point of the known template prior to computing the estimated area.

27. A non-transitory computer readable storage medium storing a set of instructions which when implemented in a medical device system cause the system to: sense a cardiac signal; derive a known template representing a known waveform morphology from the cardiac signal; compute one or more adjusted templates, each of the one or more adjusted templates computed by shifting the known template in at least one of time and amplitude; compute an upper boundary using the one or more adjusted templates; compute a lower boundary using the one or more adjusted templates, wherein an area is defined between the upper and lower boundaries; acquire an unknown waveform morphology from the cardiac signal; compare the unknown waveform morphology to the upper and lower boundaries boundary; and classify the unknown waveform morphology based on the comparison.

* * * * *